United States Patent
Nagarkatti et al.

(10) Patent No.: US 11,484,533 B2
(45) Date of Patent: Nov. 1, 2022

(54) METHODS AND COMPOSITIONS FOR TREATING OBESITY

(71) Applicant: UNIVERSITY OF SOUTH CAROLINA, Columbia, SC (US)

(72) Inventors: Prakash Nagarkatti, Columbia, SC (US); Mitzi Nagarkatti, Columbia, SC (US); Pegah Mehrpouya-Bahrami, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 16/840,513

(22) Filed: Apr. 6, 2020

(65) Prior Publication Data
US 2020/0397771 A1  Dec. 24, 2020

Related U.S. Application Data

(60) Provisional application No. 62/864,160, filed on Jun. 20, 2019.

(51) Int. Cl.
| | |
|---|---|
| *C07H 21/04* | (2006.01) |
| *A61K 31/454* | (2006.01) |
| *A61P 3/04* | (2006.01) |
| *A61K 45/06* | (2006.01) |
| *C12N 15/113* | (2010.01) |

(52) U.S. Cl.
CPC ............ *A61K 31/454* (2013.01); *A61K 45/06* (2013.01); *A61P 3/04* (2018.01); *C12N 15/113* (2013.01)

(58) Field of Classification Search
None
See application file for complete search history.

(56) References Cited

PUBLICATIONS

Bahrami, et al ("Blockade of CB1 cannabinoid receptor alters gut microbiota and attenuates inflammation and diet-induced obesity." Scientific reports 7.1 (2017): 1-16.).*
Fu et al. (Molecular and Cellular Biology, p. 4130-4142 2014).*
Alberti, et al. "Harmonizing the metabolic syndrome: a joint interim statement of the International Diabetes Federation Task Force on Epidemiology and Prevention; National Heart, Lung, and Blood Institute; American Heart Association; World Heart Federation; International Atherosclerosis Society; and International Association for the Study of Obesity" *Circulation* 120 (2009) pp. 1640-1645.
Bartel, D.P. "MicroRNAs: genomics, biogenesis, mechamsm, and function" *Cell* 116 (2004) pp. 281-297.
Becker, et al. (2018) "miR-466a targeting of TGF-β2 contributes to FoxP3+ regulatory T cell differentiation in a murine model of allogeneic transplantation" *Front. Immunol.* 9:688 (2018) pp. 1-18.
Bindea, et al. "ClueGO: a Cytoscape plug-in to decipher functionally grouped gene ontology and pathway annotation networks" *Bioinformatics* 25 (2009) pp. 1091-1093.
Cota, et al. "Food intake-independent effects of CB1 antagonism on glucose and lipid metabolism" *Obesity* 17 (2009) pp. 1641-1645.
Després, et al. "Effects of rimonabant on metabolic risk factors in overweight patients with dyslipidemia" *N. Engl. J. Med.* 353 (2005) pp. 2121-2134.
Dweep, et al. "miRWalk—database: prediction of possible miRNA binding sites by "walking" the genes of 3 genomes" *J. Biomed. Info.* 44 (2011) pp. 839-847.
Eisenstein, et al. "An adenosine receptor-Krüppel-like factor 4 protein axis inhibits adipogenesis" *J. Biol. Chem.* 289 (2014) pp. 21071-21081.
Enos, et al. "Reducing the dietary Ω-6: Ω-3 utilizing α-linolenic acid; not a sufficient therapy for attenuating high-fat-diet-induced obesity development nor related detrimental metabolic and adipose tissue inflammatory outcomes" *PLoS One* 9:e94897 (2014) pp. 1-11.
Enos, et al. "Influence of dietary saturated fat content on adiposity, macrophage behavior, inflammation, and metabolism: composition matters" *J. Lipid Res.* 54 (2013) pp. 152-163.
Esau, et al. "miR-122 regulation of lipid metabolism revealed by in vivo antisense targeting" *Cell Metab.* 3 (2006) pp. 87-98.
Esser, et al. "Obesity phenotype is related to NLRP3 inflammasome activity and immunological profile of visceral adipose tissue" *Diabetologia* 56 (2013) pp. 2487-2497.
Feig, et al. "LXR promotes the maximal egress of monocyte-derived cells from mouse aortic plaques during atherosclerosis regression" *J. Clin. Invest.* 120 (2010) pp. 4415-4424.
Gauthier, et al. (2006) "MicroRNAs: 'ribo-regulators' of glucose homeostasis" *Nat. Med.* 12 (2006) pp. 36-38.
Ge, et al. "microRNAs as a new mechanism regulating adipose tissue inflammation in obesity and as a novel therapeutic strategy in the metabolic syndrome" *J. Immunol. Res.* 2014:987285 (2014) pp. 1-10.
Gordon, et al. "Monocyte and macrophage heterogeneity" *Nat. Rev. Immunol.* 5 (2005) pp. 953-964.
Gordon, S. "Alternative activation of macrophages" *Nat. Rev. Immunol.* 3 (2003) pp. 23-35.
He, et al. "Akt-phosphorylated PIKE-A inhibits UNC5B-induced apoptosis in cancer cell lines in a p53-dependent manner" *Mol. Biol. Cell* 22 (2011) pp. 1943-1954.
Hotamisligil, et al. "Adipose expression of tumor necrosis factor-α: direct role in obesity-linked insulin resistance" *Science* 259 (1993) pp. 87-91.

(Continued)

*Primary Examiner* — Kimberly Chong
(74) *Attorney, Agent, or Firm* — Dority & Manning, P.A.

(57) ABSTRACT

The present disclosure is directed to compositions and methods for treating obesity or an inflammatory state present in obese mammals. In general, the methods and compositions disclosed herein utilize previously unrecognized miR regulatory pathways to reduce pro-inflammatory cytokine secretion and promote egress of immune cells from inflammation sites.

An example aspect of the present disclosure includes methods for treating obesity or an inflammatory state in a mammal, the method including delivering a cannabinoid receptor 1 antagonist, a Netrin-1 inhibitor, a miR inhibitor, a miR, a miR mimic, or combinations thereof to the mammal.

13 Claims, 11 Drawing Sheets
Specification includes a Sequence Listing.

(56) References Cited

PUBLICATIONS

Hwang, et al. "Sex differences in high-fat diet-induced obesity, metabolic alterations and learning, and synaptic plasticity deficits in mice" *Obesity* 18 (2010) pp. 463-469.

Jbilo, et al. "The CB1 receptor antagonist rimonabant reverses the diet-induced obesity phenotype through the regulation of lipolysis and energy balance" *FASEB J.* 19 (2005) pp. 1567-1569.

Khan, et al. "Systemic human Netrin-1 gene delivery by adeno-associated virus type 8 alters leukocyte accumulation and atherogenesis in vivo" *Gene Ther.* 18 (2011) pp. 437-444.

Klöting, et al. "MicroRNA expression in human omental and subcutaneous adipose tissue" *PLoS One* 4:e4699 (2009) pp. 1-6.

Li, et al. "Plasticity of leukocytic exudates in resolving acute inflammation is regulated by microRNA and proresolving mediators" *Immunity* 39 (2013) pp. 885-898.

Liao, et al. "Krüppel-like factor 4 regulates macrophage polarization" *J. Clin. Invest.* 121 (2011) pp. 2736-2749.

Lumeng, et al. "Obesity induces a phenotypic switch in adipose tissue macrophage polarization" *J. Clin. Invest.* 117 (2007) pp. 175-184.

Ly, et al. "Netrin-1 inhibits leukocyte migration in vitro and in vivo" *PNAS* 102 (2005) pp. 14729-14734.

Ma, et al. "MicroRNA-4661 upregulates IL-10 expression in TLR-triggered macrophages by antagonizing RNA-binding protein tristetraprolin-mediated IL-10 mRNA degradation" *J. Immunol.* 184 (2010) pp. 6053-6059.

Maianti, et al. "Anti-diabetic activity of insulin-degrading enzyme inhibitors mediated by multiple hormones" *Nature* 511 (2014) pp. 94-98.

Mantovani, et al. "The chemokine system in diverse forms of macrophage activation and polarization" *Trends Immunol.* 25 (2004) pp. 677-686.

Matthews, et al. "Homeostasis model assessment: insulin resistance and β-cell function from fasting plasma glucose and insulin concentrations in man" *Diabetologia* 28 (1985) pp. 412-419.

Medrikova, et al. "Sex differences during the course of diet-induced obesity in mice: adipose tissue expandability and glycemic control" *Int'l. J. Obes.* 36 (2012) pp. 262-272.

Mehrpouya-Bahrami, et al. "Blockade of CB1 cannabinoid receptor alters gut microbiota and attenuates inflammation and diet-induced obesity" *Sci. Rep.* 7:15645 (2017).

Miranda, et al. "MicroRNA-30 modulates metabolic inflammation by regulating Notch signaling in adipose tissue macrophages" *Int'l. J. Obes.* 42 (2018) pp. 1140-1150.

O'Rourke, et al. "Hypoxia-induced inflammatory cytokine secretion in human adipose tissue stromovascular cells" *Diabetologia* 54 (2011) pp. 1480-1490.

Odegaard, et al. "Alternative (M2) activation of Kupffer cells by PPARδ ameliorates obesity-induced insulin resistance" *Cell Metab.* 7 (2008) pp. 496-507.

Odegaard, et al. (2007) "Macrophage-specific PPARγ controls alternative activation and improves insulin resistance" *Nature* 447 (2007) pp. 1116-1120.

Ogden, et al. "Prevalence of obesity and trends in body mass index among US children and adolescents, 1999-2010" *JAMA* 307 (2012) pp. 483-490.

Perkins, et al. "Endocannabinoid system overactivity and the metabolic syndrome: prospects for treatment" *Curr. Diab. Rep.* 8 (2008) pp. 12-19.

Pi-Sunyer, et al. "Effect of rimonabant, a cannabinoid-1 receptor blocker, on weight and cardiometabolic risk factors in overweight or obese patients: RIO-North America: a randomized controlled trial" *JAMA* 295 (2006) pp. 761-775.

Ramkhelawon, et al. "Netrin-1 promotes adipose tissue macrophage retention and insulin resistance in obesity" *Nat. Med.* 20 (2014) pp. 377-384.

Rinaldi-Carmona, et al. "SR141716A, a potent and selective antagonist of the brain cannabinoid receptor" *FEBS Lett.* 350 (1994) pp. 240-244.

Rosenberger, et al. "Hypoxia-inducible factor-dependent induction of netrin-1 dampens inflammation caused by hypoxia" *Nat. Immunol.* 10 (2009) pp. 195-202.

Sacerdote, et al. "The nonpsychoactive component of marijuana cannabidiol modulates chemotaxis and IL-10 and IL-12 production of murine macrophages both in vivo and in vitro" *J. Neuroimmunol.* 159 (2005) pp. 97-105.

Sam, et al. "Rimonabant: from RIO to ban" *J. Obes.* 2011:432607 (2011) pp. 1-4.

Schäfer, et al. "The cannabinoid receptor-1 antagonist rimonabant inhibits platelet activation and reduces pro-inflammatory chemokines and leukocytes in Zucker rats" *Br. J. Pharmacol.* 154 (2008) pp. 1047-1054.

Shimizu, et al. "Semaphorin3E-induced inflammation contributes to insulin resistance in dietary obesity" *Cell Metab.* 18 (2013) pp. 491-504.

Sofia, et al. "Acute and chronic effects of δ9-tetrahydrocannabinol on food intake by rats" *Psychopharmacologia* 39 (1974) pp. 213-222.

Tacke, et al. "Monocyte subsets differentially employ CCR2, CCR5, and CX3CR1 to accumulate within atherosclerotic plaques" *J. Clin. Invest.* 117 (2007) pp. 185-194.

Taganov, et al. "NF-κB-dependent induction of microRNA miR-146, an inhibitor targeted to signaling proteins of innate immune responses" *PNAS* 103 (2006) pp. 12481-12486.

Takamatsu, et al. "Diverse roles for semaphorin-plexin signaling in the immune system" *Trends Immunol.* 33 (2012) pp. 127-135.

Van Gils, et al. "The neuroimmune guidance cue netrin-1 promotes atherosclerosis by inhibiting the emigration of macrophages from plaques" *Nat. Immunol.* 13 (2012) pp. 136-143.

Vandanmagsar, et al. "The NALP3/NLRP3 inflammasome instigates obesity-induced autoinflammation and insulin resistance" *Nat. Med.* 17 (2011) pp. 179-188.

Vejnar, et al. "miRmap: comprehensive prediction of microRNA target repression strength" *Nucl. Acids Res.* 40 (2012) pp. 11673-11683.

Wang, et al. "Effect of the cannabinoid receptor-1 antagonist rimonabant on inflammation in mice with diet-induced obesity" *Obesity* 19 (2011) pp. 505-513.

Wang, et al. "Netrin-1 overexpression protects kidney from ischemia reperfusion injury by suppressing apoptosis" *Am. J. Pathol.* 175 (2009) pp. 1010-1018.

Wang, et al. "miR-17-92 cluster accelerates adipocyte differentiation by negatively regulating tumor-suppressor Rb2/p130" *PNAS* 105 (2008) pp. 2889-2894.

Weisberg, et al. "Obesity is associated with macrophage accumulation in adipose tissue" *J. Clin. Invest.* 112 (2003) pp. 1796-1808.

Wen, et al. "Fatty acid-induced NLRP3-ASC inflammasome activation interferes with insulin signaling" *Nat. Immunol.* 12 (2011) pp. 408-415.

Yang, et al. "Epigenetic regulation of macrophage polarization by DNA methyltransferase 3b" *Mol. Endocrinol.* 28 (2014) pp. 565-574.

Yang, et al. "Weight reduction increases plasma levels of an adipose-derived anti-inflammatory protein, adiponectin" *J. Clin. Endocrinol. Metab.* 86 (2001) pp. 3815-3819.

Zhang, et al. "Expression profiles of miRNAs in polarized macrophages" *Int'l. J. Mol. Med.* 31 (2013) pp. 797-802.

Ziccardi, et al. "Reduction of inflammatory cytokine concentrations and improvement of endothelial functions in obese women after weight loss over one year" *Circulation* 105 (2002) pp. 804-809.

\* cited by examiner

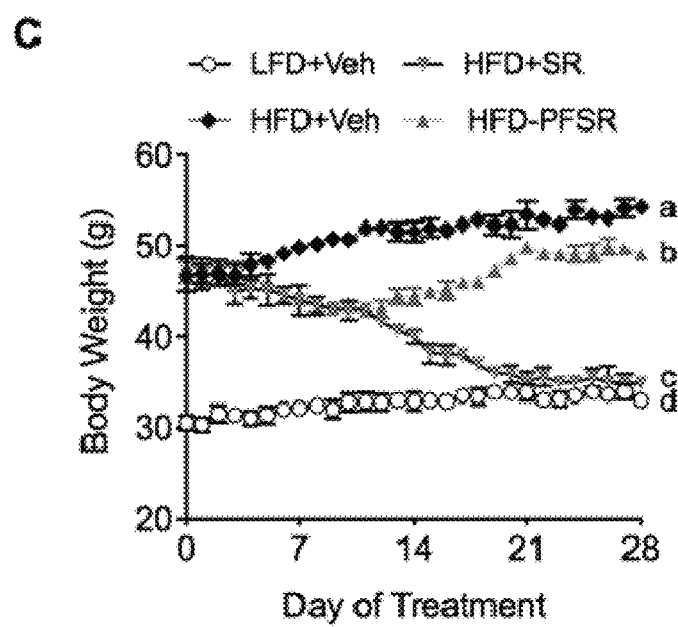
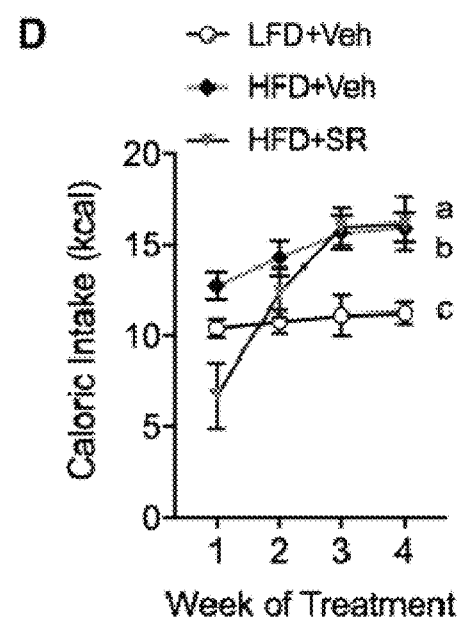
FIG. 1C
FIG. 1D

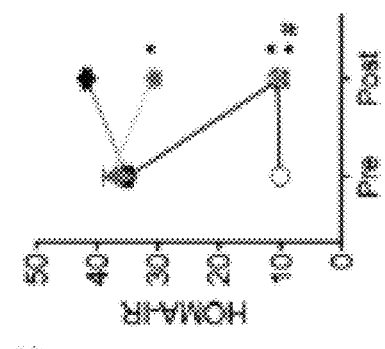
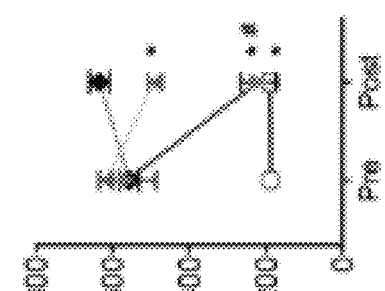
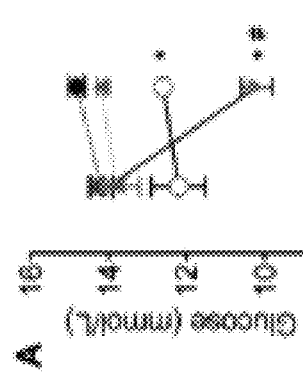
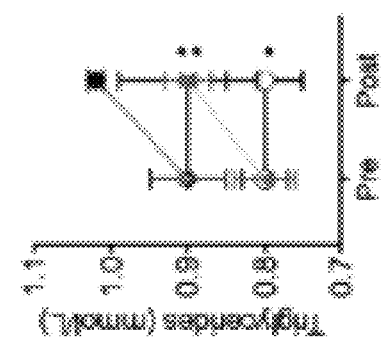
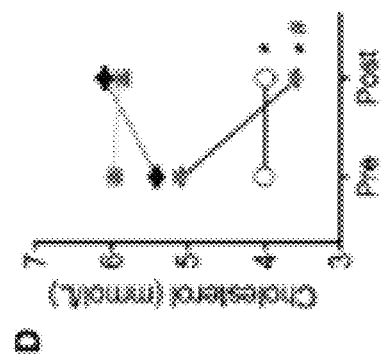

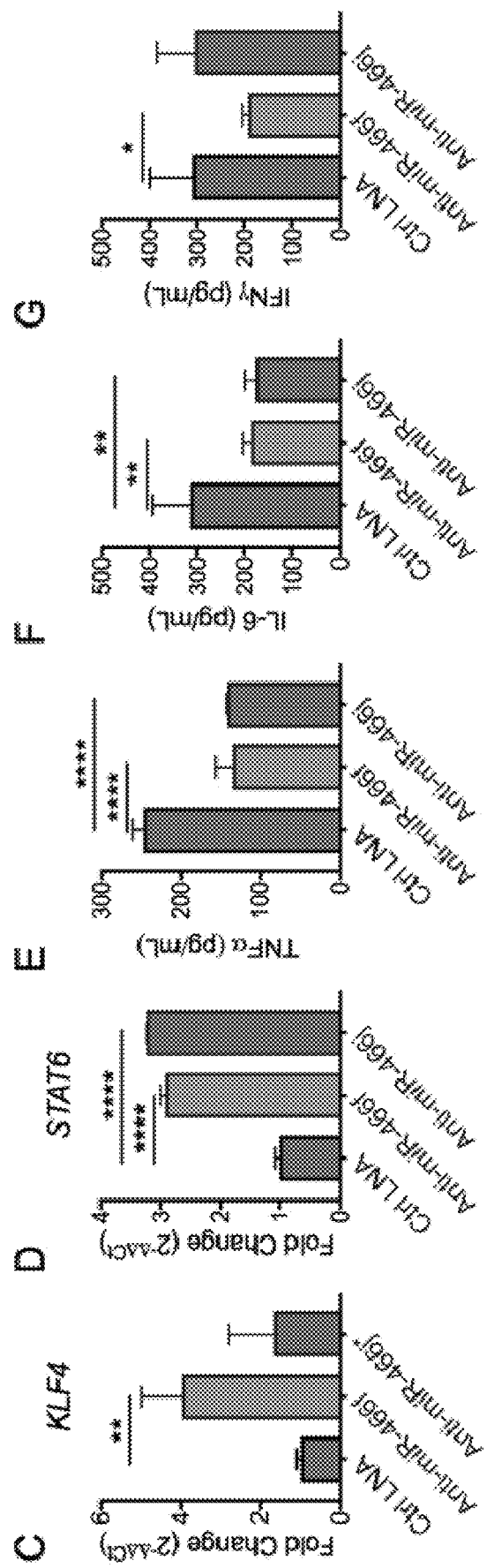

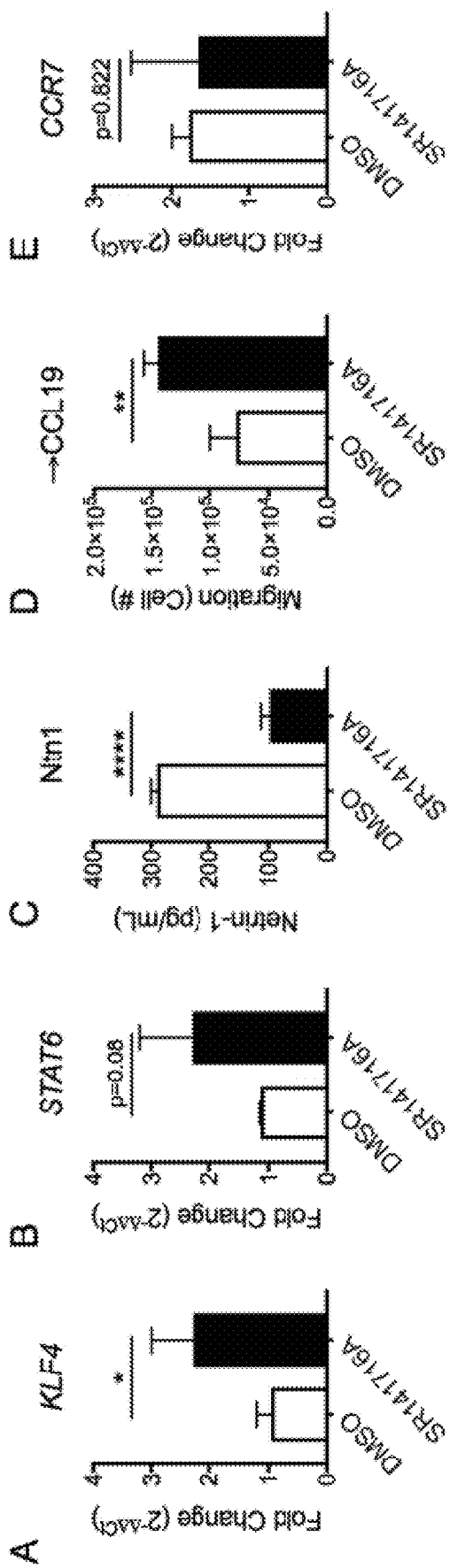

SEQUENCE LISTING

```
<160> NUMBER OF SEQ ID NOS: 7

<210> SEQ ID NO 1
<211> LENGTH: 82
<212> TYPE: RNA
<213> ORGANISM: Unknown
<220> FEATURE:
<223> OTHER INFORMATION: Description of Unknown:
      miR-762 sequence

<400> SEQUENCE: 1
ggcccggcuc cggguccucgg cccguacagu ccggccggcc augcuggcgg ggcugggccg    60
gggccgagcc cgcggcgggg cc                                              82

<210> SEQ ID NO 2
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
ccgggccgug gcccugugcc gggcutgtcu ggccggccgg tucguccgcc ccguccccgg    60
ccccggctcg ggcgccgccc cgg                                             83

<210> SEQ ID NO 3
<211> LENGTH: 84
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
ccgggccgug gcccugugcc gggcutgtcu ggccggccgg tucguccgcc ccgucccgg      60 ccccggctcg ggcgccgccc cggc                                           84

<210> SEQ ID NO 4
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (11)..(11)
<223> OTHER INFORMATION: May or may not be present

<400> SEQUENCE: 4
ccgggccgug gcccugugcc gggcutgtcu ggccggccgg tucguccgcc ccgucccgg      60 ccccggctcg ggcgccgccc cgg                                            83

<210> SEQ ID NO 5
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (9)..(9)
<223> OTHER INFORMATION: May or may not be present

<400> SEQUENCE: 5
ccgggccgua ggcccugugc cgggcutgtc uggccggccg gtucguccgc cccgucccg      60 gccccggctc gggcgccgcc ccgg                                           84

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatccgcgag atcctgat                                                  18

<210> SEQ ID NO 7
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 7
cctattggcg ttactatg                                                    18
```

METHODS AND COMPOSITIONS FOR TREATING OBESITY

CROSS REFERENCE TO RELATED APPLICATIONS

This application claims priority to U.S. Provisional Application No. 62/864,160, having the filing date Jun. 20, 2019, the entirety of which is incorporated herein by reference.

STATEMENT AS TO RIGHTS TO INVENTIONS MADE UNDER FEDERALLY SPONSORED RESEARCH

This invention was made with Government support under Contract Nos. P01AT003961, P20GM103641, R01AT006888, R01ES019313, and R01MH094755, awarded by the National Institutes of Health (NIH). The Government has certain rights in the invention.

SEQUENCE LISTING

A Sequence Listing has been filed electronically in ASCII format and is hereby incorporated by reference in its entirety. Said ASCII copy, created on Mar. 27, 2020, is named USC-623_Sequence_List.txt and is 3,613 bytes in size.

BACKGROUND

The incidence of obesity has grown significantly in the last 25 years leading to upwards of 1.45 billion overweight adults in the world, of which approximately 500 million are obese. Chronic low-grade, systemic inflammation associated with obesity plays a major role in the development of various chronic disease states, including Type-2 diabetes, metabolic syndrome, and cardiovascular disease, which together contribute to high rates of mortality and morbidity. The chronic inflammation observed is primarily driven by the intense migration and accumulation of adipose tissue macrophages (ATMs), which drive insulin resistance. The recruitment of ATMs to adipose tissue positively correlates with the production of pro-inflammatory molecules, including tumor necrosis factor-α (TNF-α), interleukin-1β (IL-1β), and IL-6, that potentiate insulin resistance.

Weight loss is associated with beneficial effects of reducing the underlying inflammation in adipose tissue and subsequent amelioration of insulin resistance. The endocannabinoid system can play a major role in food intake and energy balance. Over-activity of the endocannabinoid system in human obesity and in animal models of genetic and diet-induced obesity has been reported. Clinical studies on treatment of obesity and metabolic syndrome with the cannabinoid CB1 receptor antagonist SR141716A ("Rimonibant") have shown greater weight loss in obese patients compared with placebo. However, this drug was removed from the market due to adverse psychiatric effects. Nevertheless, the mechanistic effect of CB1 receptor antagonist on inflammation and ATMs has not been well studied. Previous studies have shown that blockade of CB1 receptors suppressed inflammation in adipose tissue of diet induced obesity (DIO) mice. However, the signals controlling the beneficial effect of the CB1 receptor antagonists on inflammation in adipose tissue remain poorly understood.

MicroRNAs (miR) are short, non-coding RNAs that can inhibit translation of their mRNA targets. Regulatory roles of miRs in many biological processes associated with obesity have been defined. They can synchronize obesity-related pathways, such as immune-mediated inflammation, insulin action, fat metabolism, and energy homeostasis. Associations between aberrant miR expression and over-activation of the endocannabinoid system in obesity have not been previously reported. Needed in the art is an understanding of the role of miRs in obesity-induced inflammation, specifically by focusing on macrophage polarization and retention in visceral adipose tissue.

SUMMARY OF THE INVENTION

The present disclosure is directed to compositions and methods for treating obesity, conditions related to obesity (e.g., Type-2 diabetes), or an inflammatory response present in obese individuals. In general, the methods and compositions utilize previously unrecognized miR regulatory pathways to reduce pro-inflammatory cytokine secretion and promote egress of immune cells from inflammation sites.

An example aspect of the present disclosure includes a method for treating obesity in a mammal, the method including delivering a cannabinoid receptor 1 antagonist, a Netrin-1 inhibitor, a miR inhibitor, a miR, a miR mimic, or combinations thereof to the mammal.

In particular, aspects of the present disclosure are not limited only to obesity treatments and can be used for treating inflammatory responses present in other disease states, either in combination with current standards of care or as a stand-alone treatment. For example, certain embodiments of the disclosure can be applied as methods to treat the inflammatory response that can present in certain diseases, autoimmune disorders, and/or transplant complications.

Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying Figures.

FIGS. 1C and 1D illustrate graphs displaying data for body weight and caloric intake, respectively, in accordance with the disclosure.

FIGS. 2A-2E illustrate graphs displaying measurements before intervention (pre) and after intervention (post) in accordance with the disclosure.

FIGS. 4C-4G illustrate change in KLF3, STATE, TNFα, IL-6, and IFNγ, respectively, on exposure to the treatment conditions shown in accordance with the disclosure.

FIGS. 6A-6E illustrate bar graphs displaying certain effects of treatment with DMSO or SR141716A in accordance with the disclosure.

Figures 1A, 1B:
FIG. 1A illustrates a timeline which shows an example treatment protocol in accordance with the disclosure.
FIG. 1B illustrates different treatment protocols developed in accordance with the disclosure.

Repeat use of reference characters in the present specification and drawings is intended to represent the same or analogous features or elements of the present invention. In general, the FIGs. included in the drawings provide examples illustrating data in support of embodiments disclosed herein.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used in combination with another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only and is not intended as limiting the broader aspects of the present invention, which broader aspects are embodied exemplary constructions.

Generally, the present disclosure is directed to methods and compositions for treating and/or reducing obesity and/or negative the health effects that can result from obesity. For example, obesity can trigger a chronic state of inflammation that can lead to the development of a disease state, such as type-2 diabetes. Aspects of treatments according to the disclosure include utilizing previously unrecognized biological pathways to induce the egress of pro-inflammatory cells from adipose tissues, alter cell-phenotype to reduce pro-inflammatory cytokine secretion, or both. As an example, a method for treating obesity according to the disclosure can include delivering one or more of the following compounds to a mammal in need thereof, the compounds including a cannabinoid receptor 1 antagonist, a Netrin-1 inhibitor, a miR inhibitor, a miR, a miR mimic, or combinations thereof.

An example cannabinoid receptor 1 antagonist can include 5-(4-chlorophenyl)-1-(2,4-dichlorophenyl)-4-methyl-N-piperidin-1-ylpyrazole-3-carboxamide, either as a hydrochloride salt (also known as Rimonabant or SR141716A) or in a neutral form. Additional antagonists in accordance with this disclosure may include antibodies or portions of antibodies targeting a non-activating epitope present on the cannabinoid receptor 1 protein. Since Rimonabant is known to have side effects that have diminished its use by medical professionals, aspects of this disclosure may provide improved treatments that demonstrate fewer side effects by targeting miR expression levels either in combination with or instead of directly targeting cannabinoid receptor 1. For instance, combination therapies using Rimonabant with miR and/or an miR inhibitor may demonstrate efficacy at lower levels of Rimonabant that would not produce as severe side effects.

For example, embodiments of the disclosure include methods and compositions for adjusting micro-RNA (miR) expression or targeting. In an example embodiment, an miR inhibitor can be included in a composition for delivery to a mammal displaying a weight problem (e.g., obesity, pre-obesity, obesity-induced diabetes, etc.). In general, the miR inhibitor can include a complementary sequence to one or more miR that were shown to be elevated in mammals fed a high-fat diet. Example miR shown to be elevated include one or more from group: miR-132-3p; miR-195a-3p; miR-34c-5p; miR-346-3p; miR-762; miR-25-3p; miR-200c-3p; miR-379-5p; miR-696; miR-714; miR-466f; miR-466h; miR-466j; miR-1940; miR-669m-5p; miR-3082-5p; miR-466m-5p; miR-3102-5p; and miR-6909-5p.

In certain instances, the miR inhibitor can be in the form of a locked nucleic acid (LNA) oligonucleotide that contains one or more nucleotide building blocks having an extra methylene bridge.

In some instances, the miR inhibitor can include a substantially complementary sequence. As an example, miR-762 includes the sequence GGCCCGGCUCCG GGU-CUCGGCCCGUACAGUCCGGCCGGCCAUGCUGGCG GGGCUGGGCCGGGGCCGA GCCCGCGGCGGGGCC (SEQ ID NO: 1) (miR sequences can be found using a database such as miRbase.org or TargetScan) which has the following complementary sequence based on nucleobase paring rules: CCGGGCCGUGGCCCUGUGCCGGGCUT-GTCUGGCCGGCCGGTUCGUCCGCCCCGUCC CCGGCCCCGGCTCGGGCGCCGCCCCGG (SEQ ID NO: 2). For embodiments of the disclosure, the substantially complementary sequence can include the complementary sequence or a modified complementary sequence. The modified complementary sequence can include one or more additions, deletions, or substitutions to modify the complementary sequence without reducing the ability to bind and inhibit the miR sequence. Using the same example complementary sequence, a substantially complementary sequence can include an addition (e.g., CCGGGCCGU GGCCCU-GUGCCGGGCUTGTCUGGCCGGCCGGTUCGU-CCGCCCCGUCCCCGGCCCCG GCTCGGGCGCCGCCCCGGC (SEQ ID NO: 3)) at one or more points in the sequence, a deletion (e.g., CCGGGCCGUG̶CCCUGUGCCGGGCUT-GTCUGGCCGGCCGGTUCGUCCGCCCC GUCCCCGGCCCCGGCTCGGGCGCCGCCCCGG (SEQ ID NO: 4)) at one or more points in the sequence, a substitution (e.g., CCGGGCCGU̶AGGCCCU GUGCCGGGCUTGTCUGGCCGGCCGGTUC GUCCGCCCCGUCCCCGGCCCCGGCTCGGGC GCCGCCCGG (SEQ ID NO: 5)) at one or more points in the sequence, or combinations of these modifications to produce the modified complementary sequence.

In some embodiments, the number of modifications that still result in inhibition can be determined using an analytical technique including, but not limited to, a circular dichroism (CD) spectrometry or calorimetry. These example techniques can also be used to determine the binding strength of an inhibitor designed to target a miR sequence, and thus, can be applied with other oligonucleotide structures such as LNA.

For embodiments of the disclosure, methods for treating obesity can be targeted to a mammalian species (e.g., a human, mouse, dog, cat, cow or sheep). As an example embodiment, a method for treating obesity in a mammal (e.g., a human) can include administering a composition to the mammal, the composition containing Rimonabant, a miR inhibitor, a miR, a miR mimic, or combinations thereof. For instance, the miR inhibitor can include a locked nucleic acid or substantially complementary sequence targeting a miR (e.g., miR-762, miR-466c, miR-466f, miR-466i, miR-466j, or other miR disclosed as elevated herein).

In certain embodiments, a miR may be included as part of the treatment. In general, the miR can include the same oligonucleotide sequence or a similar (e.g., a miR mimic) sequence for one or more miR shown to be decreased in mammals fed a high-fat diet. Example miR shown to be decreased include one or more form the following group: miR-193a-3p, miR-1947-3p, miR-3092-3p, and miR-5110.

Generally, the miR mimic can include a structure or structures similar to any of the miR disclosed herein. Development and/or structures for the miR mimics can include an artificially synthesized oligonucleotide sequence that differs in at least one base pair so that the mimic is only partially similar to the miR oligonucleotide sequence. Alternative structures for the miR mimics can include substituting uracil bases in the miR structure for thiamine bases in the mimic structure. Additional modifications to the miR structure that can produce a miR mimic may include chemically modifying a portion of the oligonucleotide structure (e.g., alkylating, acetylating, etc.), one or more hydroxyl groups, and/or one or more amine groups of the miR structure.

Alternatively, or additionally, the miR, miR mimic, miR inhibitor, or a combination thereof may be encoded as part of a vector, and the method for treating obesity in a mammal can include delivering a vector including heterologous DNA expressing one or more of the group: a miR inhibitor, a miR, a miR mimic, or combinations thereof. In this manner, a vector targeting a specific pro-inflammatory cell, such as a macrophage, may be used to direct the treatment to a certain cell type and/or an intracellular environment which may provide an advantage for certain treatments.

As an example implementation of delivering a vector, a suitable expression system for generating a substantially complementary sequence to miR-762 can be developed as a model system for producing an miR inhibitor in accordance with the disclosure. A quantity of miR-762 inhibitory oligonucleotides can be generated from this and similar expression systems. Recombinant expression is usefully accomplished using a vector, such as a plasmid. The vector can include a promoter operably linked to a sequence encoding a miR-762. The vector can also include other elements required for transcription and translation. As used herein, vector refers to any carrier containing exogenous DNA. Thus, vectors can generally refer to agents that transport the exogenous nucleic acid into a cell and can include a promoter yielding expression of the nucleic acid in the cells into which it is delivered. Vectors include, but are not limited to, plasmids, viral nucleic acids, viruses, phage nucleic acids, phages, cosmids, and artificial chromosomes. A variety of prokaryotic and eukaryotic expression vectors suitable for carrying, encoding, and/or expressing a miR-762 inhibitor are encompassed herein. Such expression vectors include, for example, pET, pET3d, pCR2.1, pBAD, pUC, and yeast vectors.

A variety of regulatory elements can be included in an expression cassette and/or expression vector, including promoters, enhancers, translational initiation sequences, transcription termination sequences, and other elements.

The expression of a miR-762 inhibitor from an expression cassette or expression vector can be controlled by any promoter capable of expression in prokaryotic cells or eukaryotic cells. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Vectors for bacterial expression include pGEX-5X-3, and for eukaryotic expression include pCIneo-CMV.

In example methods for treating obesity in accordance with the disclosure, the Netrin-1 inhibitor can include one or more compounds that target Netrin-1 for degradation or that inactivate a binding portion of the protein. For example, an antibody or a portion of an antibody (e.g., the variable region) targeting an epitope of Netrin-1 can be used as a Netrin-1 inhibitor.

Embodiments of the disclosure that provide methods for treating obesity or an inflammatory response can be used in combination with current standards of care including but not limited to immunosuppressive drugs, chemotherapeutics, non-steroidal anti-inflammatory compounds (NSAIDs), steroids and/or antibodies.

Example 1

Example 1 discusses various methods and procedures and provides exemplary embodiments that may be understood in conjunction with the Drawings and Description provided herein.

Methods

Animals, Diet and Treatment

C57BL/6J male mice (Jackson Laboratory, Bar Harbor, Me.) were fed HFD consisting of 60% Kcal from fat (D12492, Research Diets Inc, New Brunswick, N.J.) for 12 weeks before starting the intervention treatment with SR141716A. Additionally, age-matched C57BL/6J male mice were fed a low fat diet (LFD) consisting of 10% Kcal from fat (D12450J, Research Diets Inc, New Brunswick, N.J.) to develop lean controls. SR141716A was obtained from NIDA and administered at a dose of 10 mg/kg daily by oral gavage for 4 weeks, beginning after 12 weeks of diet and ending after 16 weeks. A pair-fed control group was used (HFD-PFSR) in which food intake was restricted to the amount of daily food intake of the HFD+SR group. All mice were maintained in an AAALAC-accredited animal facility at the University of South Carolina, School of Medicine (Columbia, S.C.). All procedures were performed according to NIH guidelines under protocols approved by the Institutional Animal Care and Use Committee.

Analytical Procedures

The body composition in mice was analyzed by dual-energy X-ray absorptiometry (DEXA, LUNAR, Madison, Wis.). The mice were anesthetized and placed in the prone position on the specimen tray to allow scanning of the entire body. For food intake measurements, mice were given a defined amount of large intact food pellet weekly, or daily for the HFD-PFSR group. Food weight was measured using a balance with a precision of 0.01 g. Solid food intake was corrected for any visible spillage.

Assessment of Metabolic Parameters

Measurements of blood glucose, insulin, total cholesterol, and triglycerides were performed in animals fasted for 5 hours. Blood was collected from the tip of the tail. The glucose level in whole blood was measured with a glucometer (Bayer, Leverkusen, Germany). Insulin concentration was determined in isolated plasma using an ELISA kit (Abcam, Cambridge, Mass.). Total cholesterol (Genzyme, Kent, United Kingdom) and triglycerides (Pointe Scientific, Canton, Mich.) were determined by colorimetric enzymatic reaction according to the manufacturer's instructions. To quantify insulin resistance, the homeostatic model assessment of insulin resistance index (HOMA-IR) was calculated as previously described.

Tissue Collection

After 4 weeks of treatment, mice were euthanized for tissue collection. Tissues were removed, weighed, and immediately processed to single cell suspension, snap-frozen in liquid nitrogen and stored at −80° C., or fixed in 10% formalin.

Adipocyte and Adipose Tissue Macrophage Purification

Epididymal fat pads of mice were excised and placed in gentleMACS™ C Tubes (Miltenyi Biotec, San Diego, Calif.) containing digestion medium (HBSS, 2 mg/ml collagenase (Sigma-Aldrich, St. Louis, Mo.) and 2% BSA), followed by homogenization utilizing a gentleMACS™ Dissociator (Miltenyi Biotec). After incubation at 37° C. for 30 minutes with gentle shaking, the cell suspension was filtered through a 100-μm filter and then spun at 300 g for 5 minutes to separate floating adipocytes from the stromal vascular fraction (SVF) pellet. Isolation of F4/80+ ATMs from the SVF was performed using EasySep™ FITC Positive Selection Kit (STEMCELL Technologies, Vancouver, B.C.). FITC-anti-F4/80 antibodies (Clone: BM8, BioLegend®, San Diego, Calif.) were used to label the cells for positive selection. Isolated cells were lysed for RNA analysis in QIAzol (Qiagen, Valencia, Calif.) and stored at −80° C. until RNA purification.

RNA Purification, cDNA Synthesis, and Quantitative RT-PCR

ATM RNA was isolated by miRNeasy Mini Kit (Qiagen). For RNA extraction from whole adipose tissue, 1 mg of adipose tissue was homogenized in RNA-Solv® Reagent with OBI's HiBind® technology reagent (Omega Bio-tek, Norcross, Ga.) and total RNA was isolated as previously described (31). RNA quality was verified by NanoDrop™ 2000C (Thermo Scientific™, Waltham, Mass.). Purified RNA (0.5-1 μg) was reverse-transcribed using miScript cDNA Synthesis Kit (Qiagen), and qRT-PCR analysis was conducted using SsoAdvanced™ Universal SYBR® Green Supermix kit (Bio-Rad, Hercules, Calif.). Fold change in mRNA expression was calculated using the comparative cycle method ($2^{-\Delta\Delta Ct}$).

RNA Purification, cDNA Synthesis, and Quantitative RT-PCR

ATM RNA was isolated by miRNeasy mini kit (Qiagen). For RNA extraction from whole adipose tissue, 1 mg of adipose tissue was homogenized in RNA-Solv® Reagent with OBI's HiBind® technology reagent (Omega Bio-tek, Norcross, Ga.) and total RNA was isolated as previously described (31). RNA quality was verified by NanoDrop 2000C (Thermo Scientific™, Waltham, Mass.). Purified RNA (0.5-1 μg) was reverse-transcribed using miScript cDNA Synthesis Kit (Qiagen), and qRT-PCR analysis was conducted using SsoAdvanced™ Universal SYBR® Green Supermix kit (Bio-Rad, Hercules, Calif.). Fold change in mRNA expression was calculated using the comparative cycle method ($2^{-\Delta\Delta Ct}$).

miR Expression Profiling and Analysis

The unique expression profile of miRs was assessed in F4/80+ cells isolated from adipose tissue by Affymetrix GeneChip® miR 3.0 array platform. The array contains 3100 murine-specific probes from Sanger miRBase. Total RNA was 3'-end labeled with FlashTag™ Biotin HSR hybridization technique (Genisphere, Hatfield, Pa.) and was carried out according to the manufacturer's instructions (Affymetrix®, Santa Clara, Calif.). Microarray CEL files were assessed for quality, normalized, and converted to CHP files by using the algorithm RMA-DABG in the software Affymetrix® Expression Console™ Version 1.4.1.46. CHP files were further analyzed using Affymetrix® Transcriptome Analysis Console™ Version 3.1.0.5 for annotation and differential expression. Expression of $Log_2$ fold change ($Log_2$ FC) was calculated and mean normalized expression was visualized in the form of a heat-map. miRs were considered differentially expressed if the $Log_2$ FC was greater than +/−1.95.

Bioinformatics Analysis

The differentially expressed miR target genes were assessed by miR target prediction algorithms miRwalk (http://www.umm.uni-heidelberg.de/apps/zmf/mirwalk/) and miRmap (http://mirmap.ezlab.org). To carry out an enrichment analysis of predicted target genes of miRs in biological pathways, the commercially available analysis tool, Ingenuity Pathway Analysis (IPA, Qiagen), was used. IPA predicts the top affected canonical pathways, causal connections between differentially altered miRs and their target genes, downstream effectors, and upstream regulators. The Molecular Activity Predictor (MAP) feature of IPA was performed to predict the downstream effect of the differentially expressed miRs which were overlaid to the dataset including miR probes, fold change, and p value. Gene ontology was assessed in Cytoscape platform using the ClueGo app.

ELISA Assays

TNF, IL-6, and IFNγ ELISA kits were purchased from BioLegend. Netrin-1 ELISA kits were purchased from USCN Life Science (Houston, Tex.). Concentrations were measured in cell supernatants using mouse standards according to the manufacturer's guidelines.

Migration

The migration of macrophages to CCL19 (500 ng/ml, R&D Systems) was assessed by FluoroBlock™ permeable inserts (Corning®, Tewksbury, Mass.) and Cytation™5 imaging (BioTek, Winooski, Vt.). Peritoneal macrophages were harvested from mice primed with 1 ml of 3% (wt/vol) thioglycolate (i.p.) to elicit peritoneal exudates with macrophage number peaking on day 4. Macrophages were collected in euthanized mice by intraperitoneal wash. For tracking migration towards chemoattractants, macrophages were labeled with DilC12(3) fluorescent dye (Corning®, Tewksbury, Mass.). Macrophages were treated with conditioned media from 3T3-L1 adipocytes as described and treated either with SR141716A ($10^{-6}$ M) or DMSO as the vehicle control.

Western Blot Analysis

Western blot analyses were carried out according to standard protocols with antibodies raised against Netrin-1 (R&D Systems, Minneapolis, Minn.) or γ-tubulin (Sigma-Aldrich, St. Louis, Mo.), which was used as a loading control.

Transfection and Reporter Gene Assay

Bone marrow derived macrophages (BMDM) were transfected with a plasmid containing a *Renilla* luciferase (transfection efficiency control) and 3'UTR AGAP-2 (Gene Accession: NM_001301014.1 UTR Length: 808 bp (−383-787 bp) in a Firefly luciferase reporter gene. Cloning details were as follows: The complete plasmid is 7097 bp; Vector: Pezx-MT06; Promoter: SV40, Antibiotic Ampicillin; 5' Cutting Site: AsiSI, EcoRI, BsiWI3'; Cutting Site: XhoI,SpeI with sequencing Primers (Forward: 5'-GATCCGCGAGATCCT-GAT-3' (SEQ ID NO: 6), and Reverse: 5'-CCTATTGGCGT-TACTATG-3' (SEQ ID NO: 7) (GeneCopeia™, Rockville, Md.). Cell cultures were transfected with miR-762 miR-CURY LNA™ microRNA Inhibitor (5 nM) (Exiqon, Woburn, Mass.). Lipofectamine® RNAiMAX Transfection Reagent (ThermoFisher Scientific, Waltham, Mass.) was used for delivery of oligos into the cell.

Statistical Analysis

For the in vivo mouse experiments, 10 mice were used per experimental group, unless otherwise specified. For in vitro assays, all experiments were performed in triplicate. Statistical analyses were performed using GraphPad Prism Version 7.000 (GraphPad Software, La Jolla, Calif.). Body weight, body composition outcomes, and metabolic outcomes were analyzed using a repeated measures two-way ANOVA. For statistical differences, one-way ANOVA was calculated for each experiment. Tukey's post-hoc test was performed to analyze differences between groups. A p-value of ≤0.05 was considered statistically significant.

Results

Results provided in the drawings and described herein are meant to be exemplary and are not intended to limit the methods and compositions to modifications or alternatives as would be understood by a person of ordinary skill in the field of endeavor.

SR141716A Attenuates HFD-Induced Obesity

To study the effects of CB1 antagonist on obesity parameters, DIO mice that were fed a 60% HFD for 12 weeks were treated with SR141716A (SR) by daily oral gavage for 4 weeks (FIG. 1A). All other experimental groups were treated with the vehicle (Veh) 0.1% Tween® 80. In addition to the HFD+SR group, other experimental groups included mice fed a 10% low-fat control diet (LFD) (LFD+Veh), ad-libitum HFD-fed mice (HFD+Veh), and HFD-fed mice that were pair-fed to the HFD+SR group (HFD-PFSR) (FIG. 1B). Blockade of CB1 receptors with SR141716A resulted in acute and persistent weight loss, as well as transient reduction of calorie intake in DIO mice (FIGS. 1C & 1D). At the baseline of the study, the mice were stratified into groups balanced by mean fat mass. After 4 weeks of treatment, reduction in the fat mass and fat percentage was significant in HFD+SR group when compared to both HFD+Veh and HFD-PFSR groups, while the changes in lean mass were not significant (Supplementary Table 1). Fasting parameters including blood glucose, insulin, insulin resistance index (HOMA-IR), total cholesterol and triglycerides were examined pre- and post- the 4-week intervention with SR compound. Our data demonstrated improvement in metabolic parameters in the HFD+SR group when compared to HFD+Veh and HFD-PFSR (FIGS. 2A-2E). Taken together, our data suggested that blocking CB1 receptors in DIO mice results in amelioration of obesity, independent of its effect on calorie intake.

SR141716A Reduces Adipose Tissue Inflammation and Alters ATM miR Profile

Figure 3A:
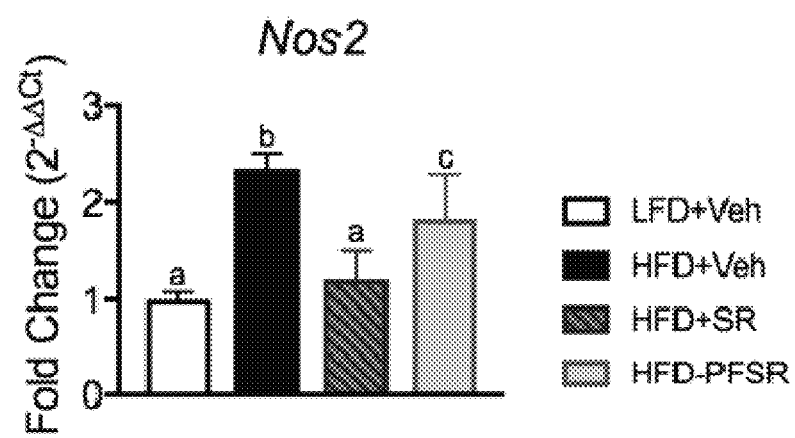
FIGS. 3A and 3B illustrate bar graphs displaying fold change for Nos2 and Arg1, respectively, for the conditions shown in accordance with the disclosure.
Figure 3B:
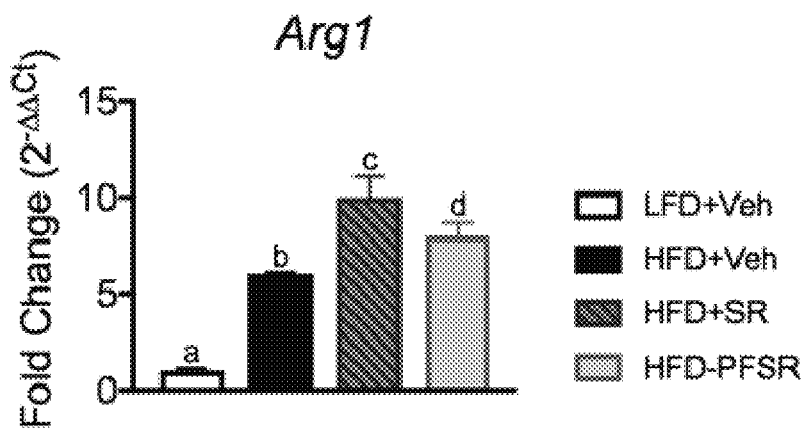

A previous report showed that treatment of DIO mice with SR reduces both ATM infiltration and M1 polarization in epididymal adipose tissue. To further confirm the overall inflammatory status in adipose tissue, the expression of macrophage polarization was quantified for genes Nos2 (M1) and Arg1 (M2) in epididymal fat. SR treatment lowered Nos2 expression and increased expression of Arg1, which validated an anti-inflammatory state in the adipose tissue of DIO mice following SR141716A treatment (FIGS. 3A-3B).

Figure 3C:
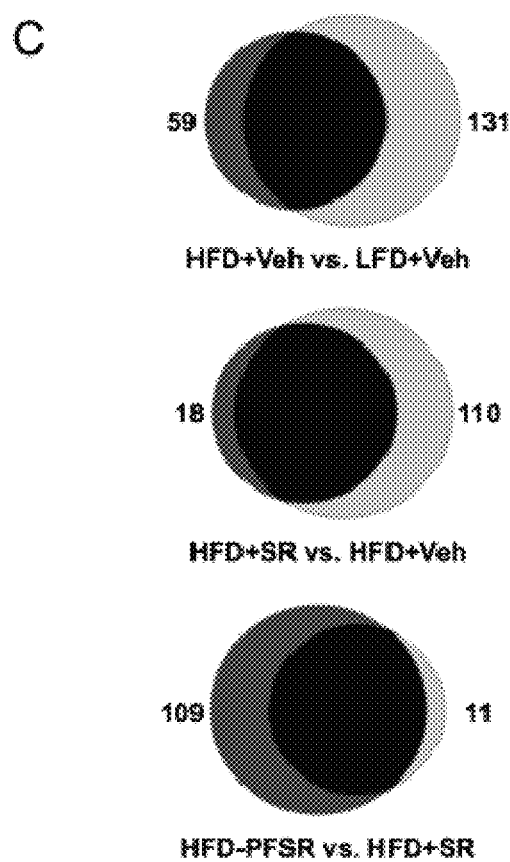
FIG. 3C illustrates a Venn diagram comparing expression levels for the conditions shown in accordance with the disclosure.

Next, to determine if SR treatment alters miR expression in ATMs, miR microarray analyses were performed in F4/80+ cells isolated from the stromal vascular fraction of epididymal adipose tissue. Of the more than 3000 miRs tested, 18 were over-expressed and 110 were under-expressed greater than or equal to ±1.95 $\log_2$ fold-change in the HFD+SR group when compared to the HFD+Veh group, while 11 and 109 of miRs were significantly up- and down-regulated respectively in HFD+SR vs. HFD-PFSR group (FIG. 3C). In addition, 59 up- and 131 down-regulated miRs were identified in HFD+Veh vs. LFD+Veh (FIG. 3C).

Figure 3D:
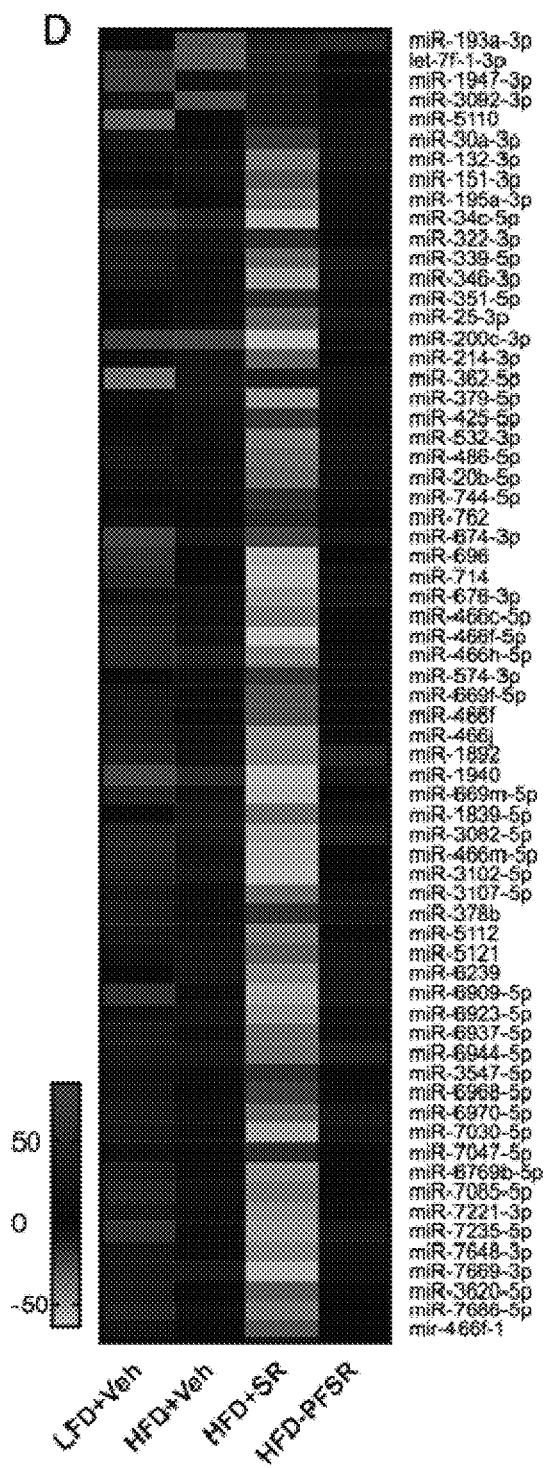
FIG. 3D illustrates a heat map displaying miR expression for the conditions shown in accordance with the disclosure.

In order to investigate the effect of SR141716A on miR profile independent of its effect on calorie restriction, miRs that were similarly dysregulated in both HFD+SR vs. HFD+Veh and HFD+SR vs. HFD-PFSR groups were identified. A heatmap of mean normalized expression of these altered miRs demonstrated that SR treatment alters miR expression independent of food restriction (FIG. 3D).

We next used in silico analyses to identify potential pathways targeted by the dysregulated miRs. First, using Cytoscape analysis modules, the targeted gene ontologies of dysregulated miRs were identified. The main affected pathways following SR treatment included regulation of various components of the immune system (Supplementary FIG. 1). Next, analysis using Ingenuity Pathway Analysis (IPA, Qiagen) was performed. Predicted interactions between miRs and their targeted genes following SR treatment revealed that the altered miR profile might skew the ATM balance to a more anti-inflammatory macrophage phenotype (M2, Arginase+) (Supplementary FIG. 2).

SR141716A-Altered miRs Promote a Shift Towards M2 Macrophage Phenotype

Figure 4A:
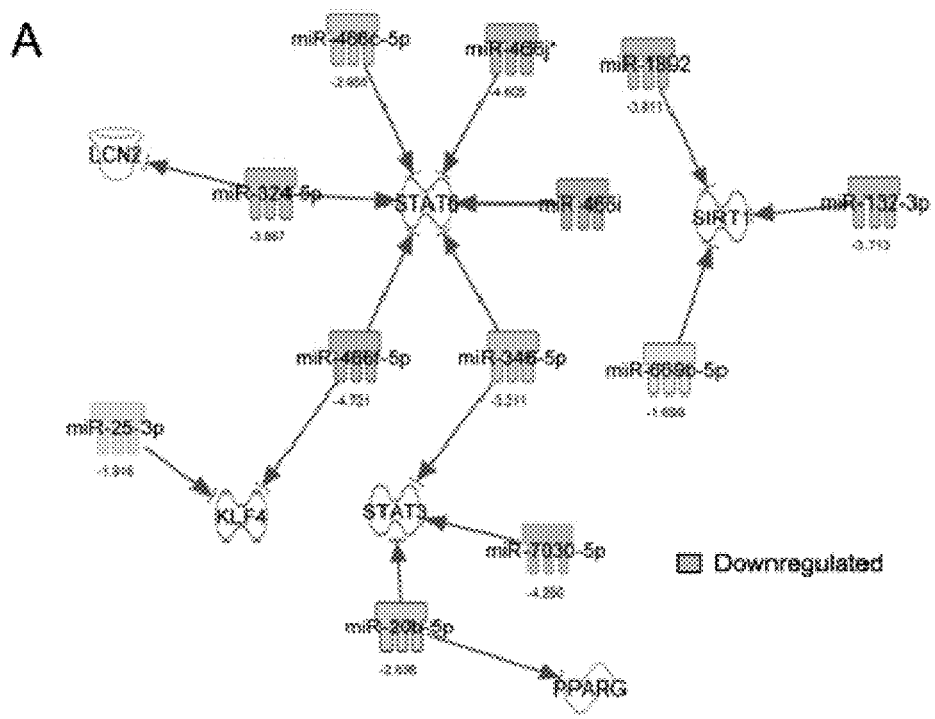
FIG. 4A illustrates a map of miR and predicted gene targets in accordance with the disclosure.
Figure 4B:
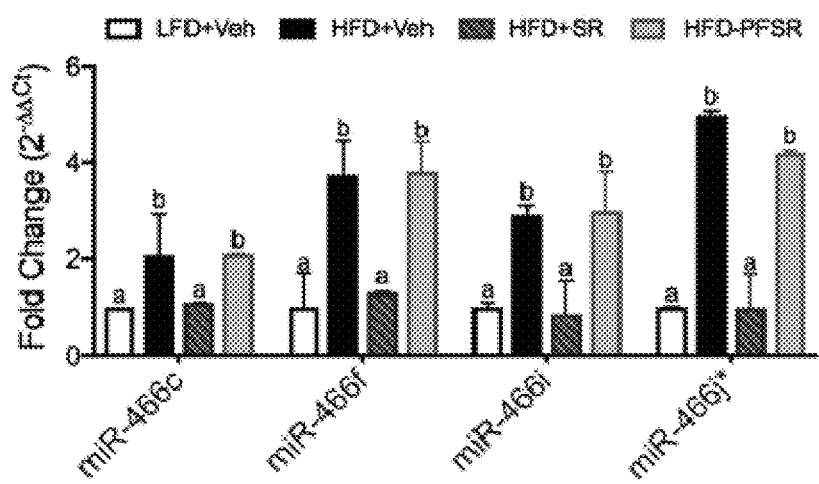
FIG. 4B illustrates a bar graph of miR expression for the conditions shown in accordance with the disclosure.

Interestingly, pathway analysis with IPA uncovered SR141716A-mediated alterations in miRs that may induce anti-inflammatory M2 macrophages by targeting the M2 related transcription factors (STAT3, STATE, LCN2, KLF4, PPARg, SIRT1) (FIG. 4A). The list of corresponding targets and miRs, along with each algorithm is summarized in Supplementary Table 2. More interestingly, for the first time it was uncovered that most of the members of the miR-466 family were down-regulated following SR141716A treatment regardless of calorie intake (FIGS. 3D and 4A). qRT-PCR of the miR-466 family from the ATMs validated that these were down-regulated following SR141716A treatment (FIG. 4B).

In order to validate the impact of the miR-466 family in induction of M2 phenotype in ATMs, peritoneal macrophages were isolated and cultured in conditioned medium from differentiated 3T3-L1 adipocytes, following transfection with miR-466j* and miR-466f LNA™ power inhibitors. The data showed that KLF4 and STAT6 were overexpressed following miR-466 inhibition (FIGS. 4C and 4D), thereby suggesting that miR-466 targeted these transcription factors. Moreover, the inflammatory cytokines such as TNF-α, IL-6 and IFN-γ were suppressed following miR-466 inhibition (FIGS. 4E-4G). Taken together these data suggested that blockade of CB1 in DIO mice results in down-regulation of the miR-466 family in ATMs, which promotes M2 macrophage polarization and thereby induces a switch towards anti-inflammatory state in adipose tissue.

SR141716A Ameliorates ATM Retention in Adipose Tissue

Figure 5A:
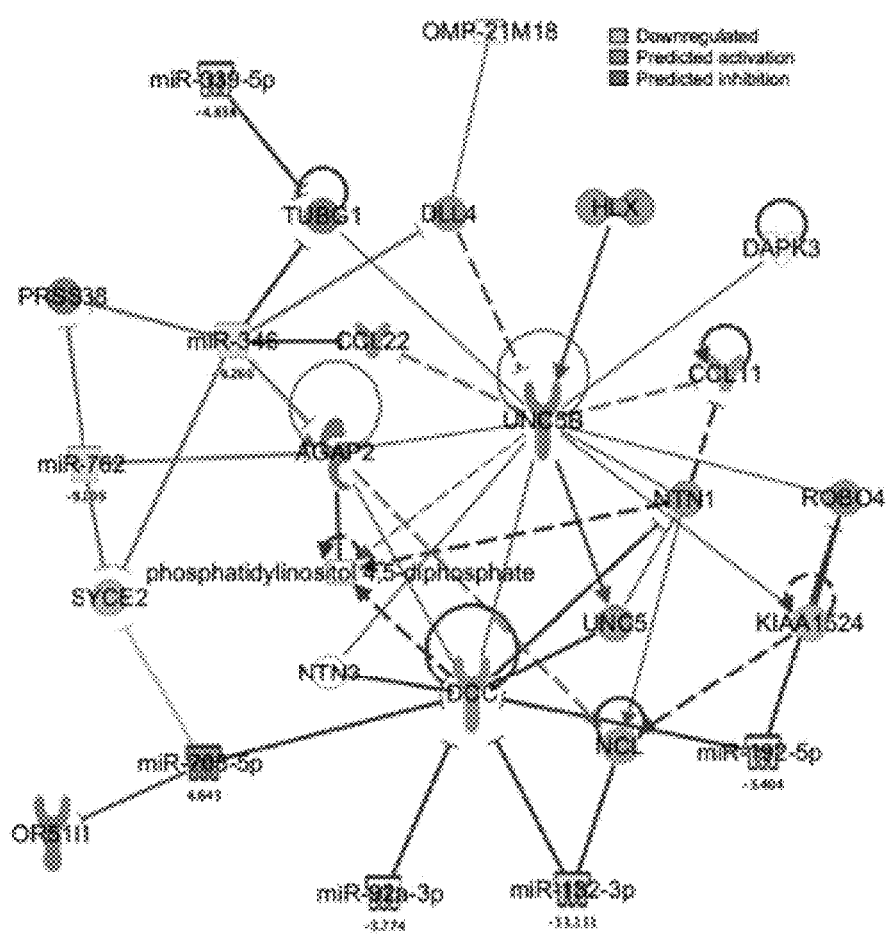
FIG. 5A illustrates a map of miR and predicted gene targets in accordance with the disclosure.
Figure 5B:
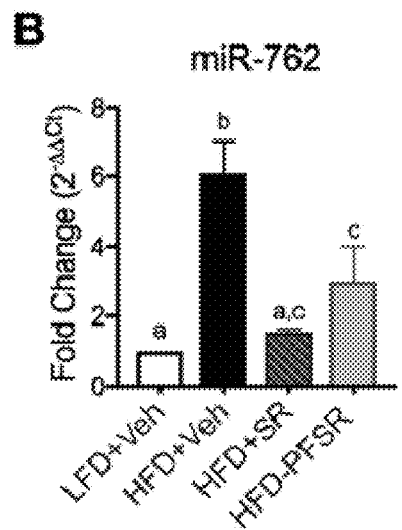
FIGS. 5B and 5C illustrate bar graphs displaying the fold change in miR-763 and Agap2, respectively, on exposure to the treatment conditions shown in accordance with the disclosure.
Figure 5C:
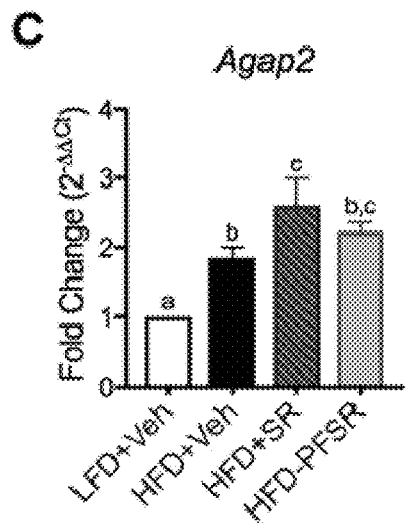
Figure 5D:
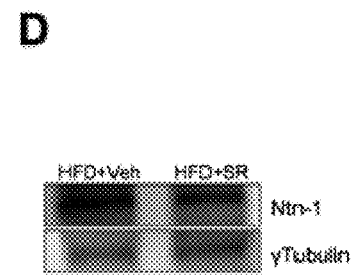
FIG. 5D illustrates a Western Blot gel stained for the proteins indicated on exposure to the treatment conditions shown in accordance with the disclosure.
Figure 5E:
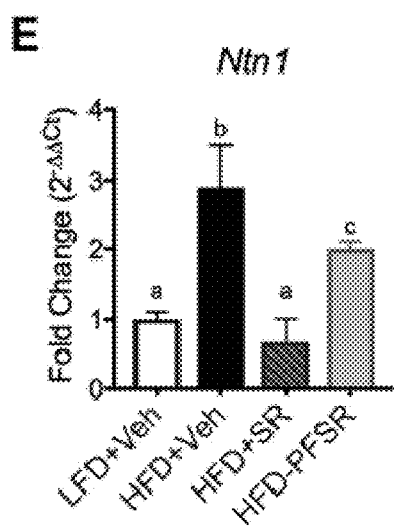
FIGS. 5E-5G illustrate bar graphs displaying the fold change in Ntn1, Unc5b, and Agap2 3'UTR on exposure to the treatment conditions shown in accordance with the disclosure.
Figure 5F:
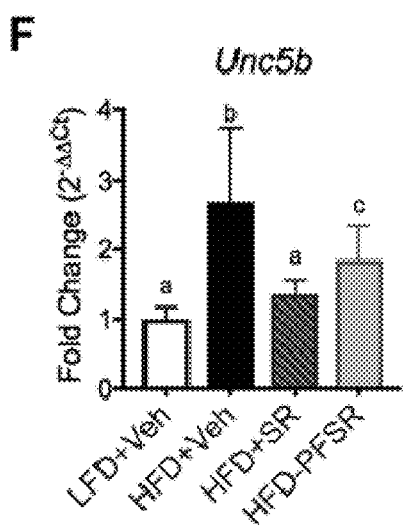
Figure 5G:
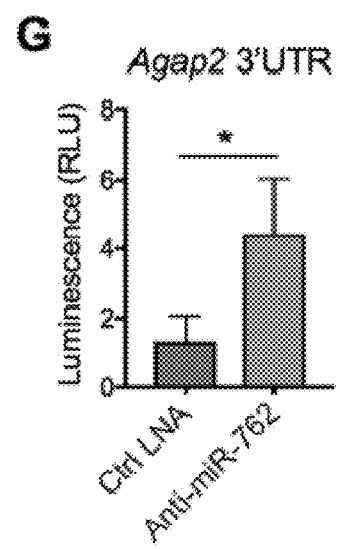

In addition to the effect of SR141716A in promoting M2 macrophages, it had been previously demonstrated significant decrease in the number of pro-inflammatory M1 macrophages in adipose tissue of the HFD+SR treated group when compared to the HFD+Veh group. The current study investigated if this resulted from altered migration of ATM due to miR-mediated regulation of neuronal guidance cues. Filtering the IPA modules to the neuroimmune guidance cue canonical pathways demonstrated a novel series of miRs that targeted AGAP2, which is an upstream negative regulator of the Netrin-1 receptor UNC-5 Homology B (UNC5B) (FIG. 5A). This suggested that downregulation of miR-762 may increase AGAP-2, and thus inhibit Netrin-1-mediated ATM detainment (FIG. 5A). qRT-PCR validated expression of miR-762 was reduced while Agap2 was increased following SR treatment (FIGS. 5B and 5C). Interestingly, the level of expression of Netrin-1 at both protein and transcription level in ATM was significantly reduced in HFD+SR mice when compared to HFD+Veh mice (FIGS. 5D and 5E). Unc5b was also downregulated in the HFD+SR vs. HFD+Veh (FIG. 5F). To validate the direct interaction of miR-762 and AGAP-2, BMDM that were treated with conditioned medium from 3T3-L1 adipocytes were used. Such BMDMs were transfected with a *Renilla* luciferase plasmid (transfection efficiency control) containing the 3'UTR of Agap2 and a Firefly luciferase reporter gene. Luciferase expression was suppressed by endogenous miR-762. Subsequently, upon transfection with Anti-miR-762 LNA microRNA inhibitor (5 nM), increased luciferase activity/luminescence was detected thereby demonstrating that the Agap2 3'UTR is a direct target of miR-762 (FIG. 5G).

Macrophage-Dependent CHI Blockade Promotes M2 Polarization and Decreased Retention Next, to confirm that the M2 polarization and decreased ATM retention observed in HFD+SR treated mice was a direct effect of CB1 blockade and not a secondary effect due to weight loss or other factors, primary macrophages were treated in vitro with 3T3-L1 adipocyte conditioned media and SR141716A or DMSO vehicle control. Treatment of BMDM with adipocyte conditioned medium and SR141716A led to induction of Klf4 and Stat6 (FIGS. 6A and 6B). Netrin-1 secretion was also reduced following SR141716A treatment (FIG. 6C). These findings confirmed that blockade of macrophage CB1 signaling has anti-inflammatory effects.

Furthermore, the decreased expression of Netrin-1 mediated by SR141716A in vivo suggested that this would lead to loss of macrophage accumulation in the adipose tissue. To test this, thioglycollate-elicited peritoneal macrophages were isolated and cultured them in 3T3-L1 adipocyte conditioned medium and treated them with SR141716A or vehicle. Their migration rate towards CCL19 was measured because CCL19 is the primary chemokine implicated in emigration of tissue macrophages towards draining lymph nodes. Notably, SR141716A-treated macrophages exhibited higher migration towards CCL19 than DMSO-treated macrophages (FIG. 6D), though the level expression of CCL19 receptor, CCR7, was similar in both groups (FIG. 6E). These data suggested that SR141716A attenuates the over-secretion of Netrin-1 from ATMs in obese phenotype, and potentially promotes their emigration from adipose tissue.

The invention claimed is:

1. A method for treating obesity in a mammal comprising: delivering a miR inhibitor to the mammal, wherein the miR inhibitor inhibits one or more members of the miR-466 family or inhibits miR-762.

2. The method of claim 1, wherein the miR inhibitor comprises a substantially complementary sequence to one or more of the following: miR-466f, miR-466h, miR-466j, or miR-466m 5p.

3. The method of claim 1, wherein the mammal is selected from one of the group consisting of a human, an ape, a monkey, a mouse, a rat, and a dog.

4. The method of claim 1, further comprising delivering at comprising:
   delivering a vector including heterologous DNA expressing the miR inhibitor.

5. The method of claim 4, wherein the miR inhibitor comprises a substantially complementary sequence to one or more of the following: miR-466f, miR-466h, miR-466j, miR-466i, miR-466c, or miR-762.

6. The method of claim 4, further comprising delivering 5-(4-chlorophenyl)-1-(2,4-dichlorophenyl)-4-methyl-N-piperidin-1-ylpyrazole-3-carboxamide to the mammal.

7. The method of claim 4 wherein the vector comprises: a plasmid, a viral nucleic acid, a virus, a phage nucleic acid, a phage, a cosmid, or an artificial chromosome.

8. The method of claim 1, wherein the miR inhibitor comprises a miR-466j inhibitor.

9. The method of claim 1, wherein the miR inhibitor comprises a miR-466f inhibitor.

10. The method of claim 1, wherein the miR inhibitor comprises a miR-466c inhibitor.

11. The method of claim 1, wherein the miR inhibitor comprises a miR-466i inhibitor.

12. The method of claim 1, wherein the miR inhibitor comprises a miR-762 inhibitor.

13. The method of claim 1, wherein the miR inhibitor comprises a locked nucleic acid oligonucleotide.

\* \* \* \* \*